(12) United States Patent
Peecock et al.

(10) Patent No.: US 7,856,889 B2
(45) Date of Patent: Dec. 28, 2010

(54) HIGH SPEED PULL TEST DEVICE AND METHOD

(75) Inventors: Benjamin Kingsley Stuart Peecock, Suffolk (GB); Alan Norman Wiltshire, Essex (GB)

(73) Assignee: Nordson Corporation, Westlake, OH (US)

( * ) Notice: Subject to any disclaimer, the term of this patent is extended or adjusted under 35 U.S.C. 154(b) by 601 days.

(21) Appl. No.: 10/599,153

(22) PCT Filed: Mar. 17, 2005

(86) PCT No.: PCT/GB2005/001116

§ 371 (c)(1),
(2), (4) Date: Aug. 22, 2007

(87) PCT Pub. No.: WO2005/093436

PCT Pub. Date: Oct. 6, 2005

(65) Prior Publication Data

US 2008/0257059 A1  Oct. 23, 2008

(30) Foreign Application Priority Data

Mar. 22, 2004  (GB) ................... 0406434.1

(51) Int. Cl.
*G01N 3/08* (2006.01)
(52) U.S. Cl. ...................................... 73/827
(58) Field of Classification Search ............ 73/827; 257/48
See application file for complete search history.

(56) References Cited

U.S. PATENT DOCUMENTS

| | | | | |
|---|---|---|---|---|
| 5,144,845 | A | * | 9/1992 | Pyke .............................. 73/827 |
| 5,401,911 | A | * | 3/1995 | Anderson et al. ............ 174/262 |
| 5,948,997 | A | * | 9/1999 | Schmidt ................... 73/862.08 |
| 6,078,387 | A | | 6/2000 | Sykes |
| 6,358,627 | B2 | * | 3/2002 | Benenati et al. ............. 428/612 |
| 6,564,115 | B1 | | 5/2003 | Kinnaird |
| 6,564,648 | B2 | * | 5/2003 | Lee et al. ....................... 73/842 |
| 6,584,858 | B1 | * | 7/2003 | Miyazawa et al. ............ 73/827 |
| 6,912,915 | B2 | * | 7/2005 | Jian et al. ....................... 73/827 |
| 7,329,900 | B2 | * | 2/2008 | Yeh et al. ....................... 257/48 |
| 7,389,698 | B2 | * | 6/2008 | Hutter, III .................... 73/827 |
| 2004/0103726 | A1 | * | 6/2004 | Cox .............................. 73/842 |

FOREIGN PATENT DOCUMENTS

| | | |
|---|---|---|
| EP | 0 772 036 | 5/1997 |
| WO | WO 2004/083831 | 9/2004 |

OTHER PUBLICATIONS

The International Search Report for PCT Application No. PCT/GB2005/001116; Filed Mar. 17, 2005; Date of Completion Jan. 11, 2006; Date of Mailing Jan. 18, 2006.

* cited by examiner

*Primary Examiner*—Lisa M Caputo
*Assistant Examiner*—Octavia Davis
(74) *Attorney, Agent, or Firm*—Wood, Herron & Evans, L.L.P.

(57) ABSTRACT

A device and method for tensile testing of the bond strength of an electrically conductive ball adhered to a substrate. A ball is gripped and moved at a speed in a direction substantially orthogonal to the plane of adherence. The substrate is abruptly halted by an abutment to impose a sudden load on the ball/substrate interface. During the test the substrate is lightly urged toward the ball to eliminate unwanted tensile forces.

18 Claims, 2 Drawing Sheets

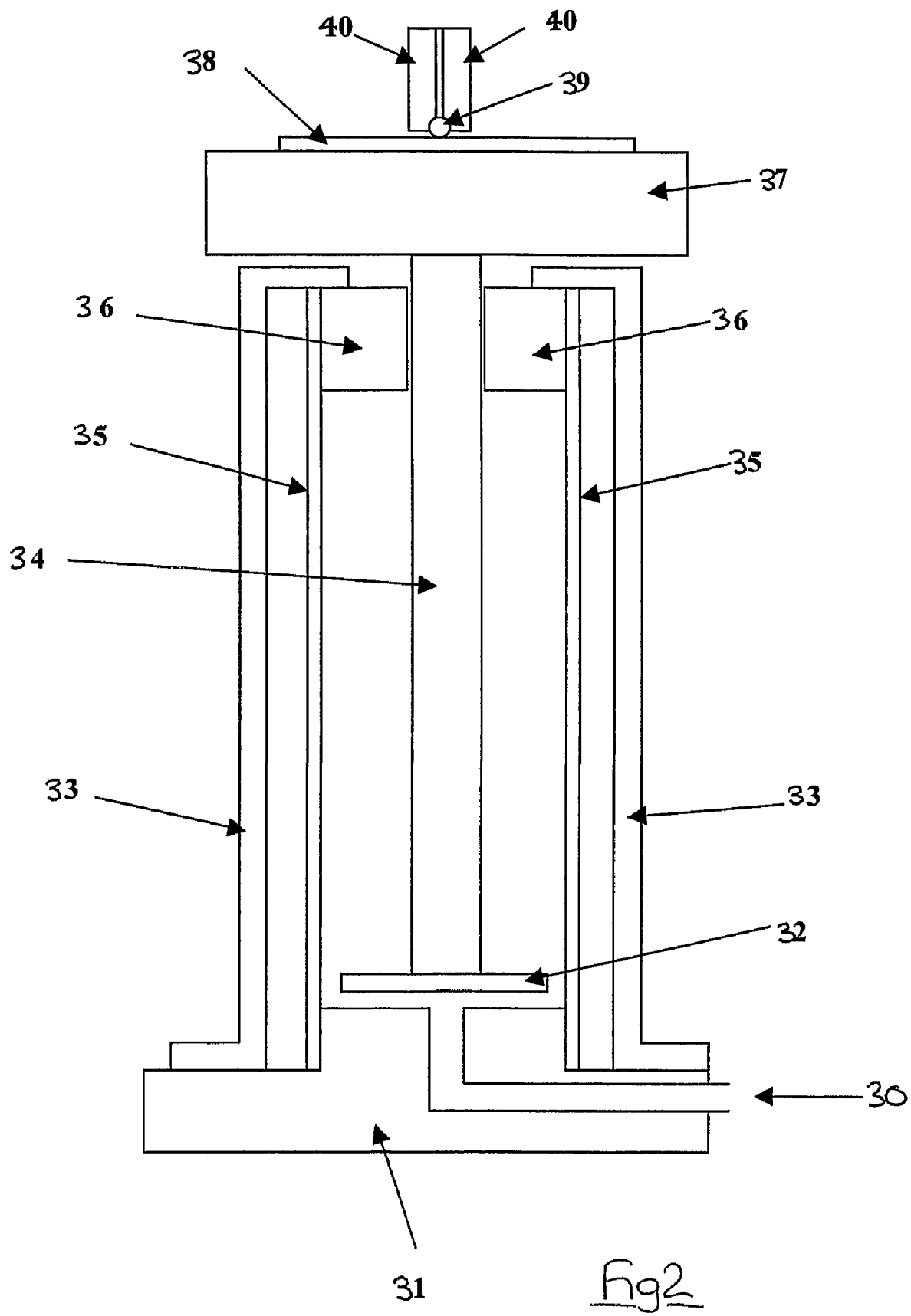

HIGH SPEED PULL TEST DEVICE AND METHOD

BACKGROUND OF THE INVENTION

This invention relates to a test device for electrical bonds of semi-conductors, and particularly to a device and method suitable for high speed pull testing.

Electrical bonds of semi-conductor devices often comprise an array of solder or gold balls, on a substrate having electrical pathways. These balls are used to connect individual wires to the pathways, or to connect to pathways of another substrate whilst the substrates are in aligned contact. A solder ball will be re-flowed, and a gold ball will be welded.

Test devices are required to confirm that the balls have sufficient mechanical adhesion to the substrate, in order to confirm viability of the manufacturing technique. It is known to test in shear by driving a tool at the side of a ball, and in tension by gripping and pulling the ball orthogonally to the substrate.

The individual balls are generally arranged in an array, and are very small. A solder ball is typically in the range 1000-75 µm in diameter, whereas a gold ball is in the range 100-20 µm in diameter. These 'balls' have a somewhat hemispherical appearance when attached to a substrate. The very small size of some solder and gold balls means that the breaking forces are very low, and special measures are required to reduce friction to a minimum so as to permit breaking force to be measured.

Testing of the ball/substrate bond at a high rate of stress is desirable. In the case of a shear test, the tool can be driven against the respective ball from a distance, and thus the necessary impact speed can be generated. However high speed pull testing of balls is problematic because the test tool must first grip the ball, and thus cannot gather speed or momentum before the test commences.

BRIEF SUMMARY OF THE INVENTION

The present invention provides one solution to the problem of high speed pull testing. According to one aspect of the invention there is provided a method of testing an electrically conductive ball adhered to a substrate, and comprising the steps of gripping the ball with a test tool, moving the ball in a direction substantially orthogonal to the substrate whilst urging the substrate lightly against the ball, and abruptly halting the substrate.

The substrate is lightly supported so as to impose very little gravitational or inertial force on the bond between the ball and the substrate. When the substrate stops, the insertion of the test tool causes a shock load to be exerted on the ball, and hence on the ball/substrate interface. In a preferred embodiment the test tool pulls the ball, and light support is for example provided by a light spring or an air ram. An air ram may be preferable because it has a substantially constant rate.

In a preferred embodiment the substrate is halted by a fixed abutment of a test machine having a frame with respect to which the test tool is movable. Preferably the method commences with the substrate in contact with the abutment, and the test tool is advanced against the light support so as to push the substrate away from the abutment to a position from which the test tool is reversed at speed, thus bringing the substrate into abrupt contact with the abutment.

This arrangement is advantageous since it permits the substrate to be restrained during gripping, and allows the speed of the test tool at the point of restraint of the substrate to be adjusted, according to the distance over which the tool accelerates, or according to the rate of change of acceleration over a fixed distance.

The arrangement may also be used for a static pull test in which the substrate is in contact with the abutment prior to pulling on the ball.

According to a second aspect of the invention there is provided apparatus for tensile testing of an electrically conductive ball adhered to a substrate, the apparatus comprising a gripper for gripping a ball adhered to a substrate, a platen having a surface for supporting the substrate, means for moving the gripper on an axis substantially orthogonal to said surface, means to lightly urge the platen on said axis towards the gripper, and an abutment for the substrate whereby, in use, the platen and gripper move in unison with respect to the abutment until the substrate contacts the abutment, whereby the gripper and platen tend to move apart.

This apparatus permits sudden application of force to the ball/substrate interface. Conventional means may be provided to permit the breaking load to be determined.

The substrate may be arrested directly by contact with an abutment of a machine frame, or may be clamped to e.g. a platen so that the platen (or a connected part thereof) is arrested to indirectly arrest the substrate.

Preferably means are provided to drive the gripper with respect to a fixed abutment. The means to lightly urge the platen toward the gripper may be for example a light spring or an air ram. The urging force required is just sufficient to avoid drag on the substrate, such as might be imposed by gravitational frictional or inertial forces.

BRIEF DESCRIPTION OF THE DRAWINGS

Other features of the invention will be apparent form the following description of a preferred embodiment shown by way of example only in the accompanying drawings in which:—

FIG. 2 is a schematic side elevation of test apparatus according to a second embodiment of the invention.

Figure 1:
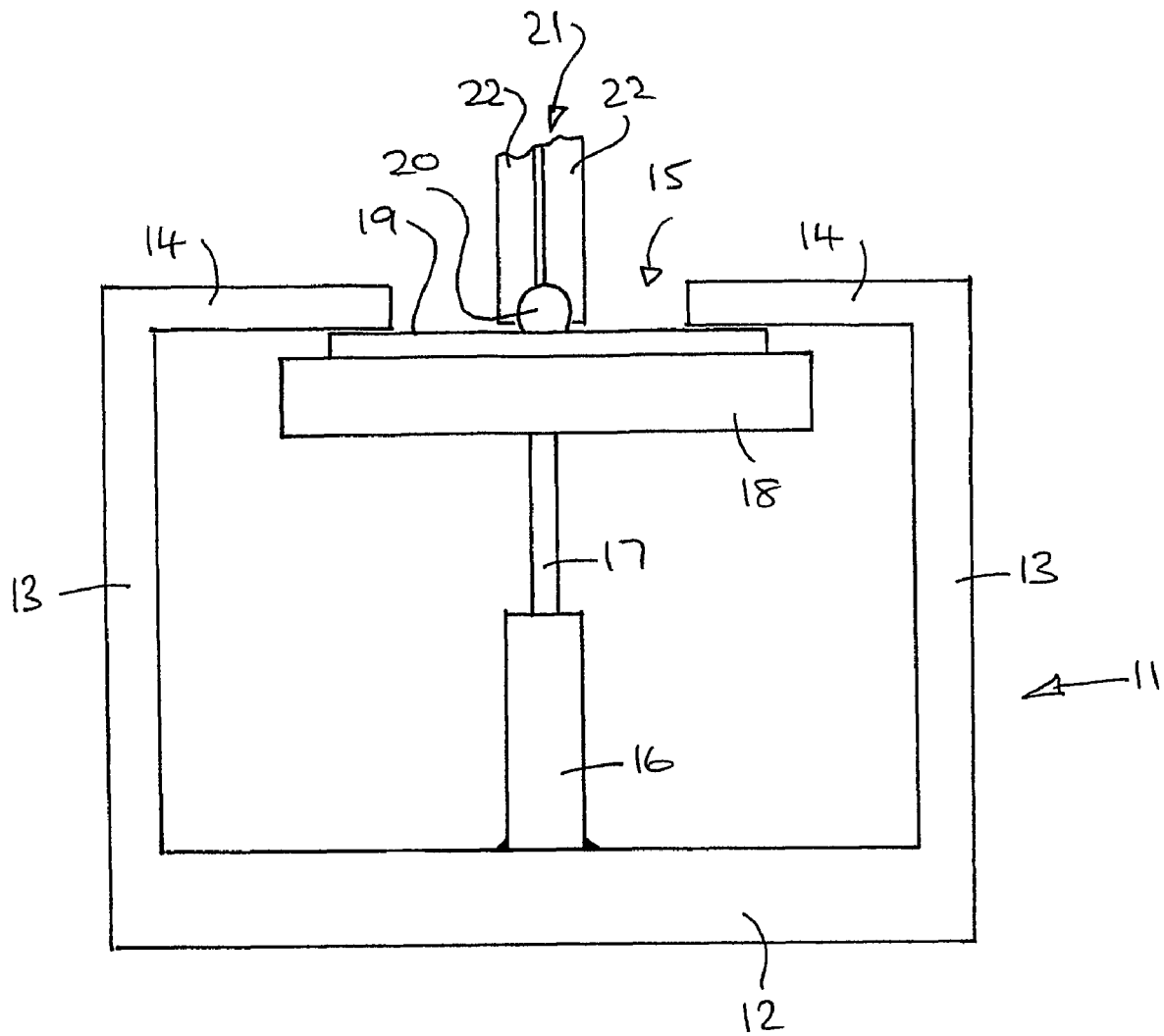
FIG. 1 is a schematic side elevation of test apparatus according to a first embodiment of the invention.

The proportions illustrated in the drawings are exaggerated for the purposes of clear understanding of the invention. In particular it must be remembered that the solder ball illustrated is typically around 100 µm in diameter

DETAILED DESCRIPTION OF THE DRAWINGS

With reference to the drawings a rigid frame 11 comprises a base 12 with upstanding legs 13 at each side, each leg having an inwardly directed arm 14 in a common plane, and defining an opening 15 therebetween.

Centrally located on the base is an air actuator 16 having a ram 17 on which is situated a platen 18. A substrate 19 having a solder ball 20 rests on the platen 18, and at its edges is in contact with the inner side of the arms 14, as illustrated.

Typically a substrate will have a plurality of balls thereon and provided in a regular array. In a preferred embodiment the test tool is indexable to engage a desired ball, for example by use of a conventional X-Y axis drive. Furthermore the apparatus may include machine vision means to allow positioning of the test tool over successive balls.

A pull test tool 21 has opposite jaws 22 which are adapted to open and close about the ball 20, and which is movable orthogonally to the platen 18 to apply a tensile test to the ball.

In use the substrate 19 is positioned on the platen 18 as illustrated, and lightly urged against the arms 14 by the ram 17.

The test tool 21 is driven down over the ball 20 and the jaws closed, so that the ball is gripped. The test tool is then driven down further against the ram 17 so that the substrate is at a distance from the arms 14.

The actuator may have a permanent leak path to permit the ram to retreat without exerting substantive force on the platen.

The test is performed by accelerating the test tool 21 upward, allowing the ram 17 to follow, at all times keeping the platen in contact with the substrate.

At a desired speed the substrate makes contact with the arms and is immediately stopped. However the test tool continues upward, and by virtue of its grip on the ball can apply a sudden jerk to the ball/substrate interface. By this means the apparatus allows a high speed tensile test to be performed for the purpose of measuring the breaking force of the ball/substrate interface. The breaking force is measured by known apparatus.

The illustrated apparatus is diagrammatic, and only one ball is illustrated on the substrate. In practice an array of balls would be present, and means provided to allow either the test head or the frame to be indexed, so as to place the required ball under the test tool. For example the frame 11 could be placed on a conventional movable X-Y table.

The frame may of course having a single upstanding peripheral wall in place of legs 13, and circumferentially extending arms. If required conventional means of locating and holding the substrate with respect to the platen may also be provided.

The force exerted by the ram 17 must be sufficient to avoid any tensile load on the bond/substrate interface whilst the ram is moving upward. This force can be determined empirically and the ram force may for example be adjusted by a variation in air pressure supplied thereto. Other conventional means of supporting the platen 18 may be provided, for example a light spring, in place of the actuator 16.

An alternative embodiment is illustrated in FIG. 2. In this embodiment upward movement of the ram is arrested on internal abutment. As a consequence there is nothing standing proud of the sample.

In detail, a base 31 supports an upstanding guide tube 35 which has at its mouth a annular guide 36 within which slides a piston rod 34. The piston rod has a large orthogonal foot 32 which lies over an inlet of a compressed air supply 30.

The guide tube is held in place by a clamp tube 33 which is for example bolted via an external flange to the base 31, and has an internal flange engaging over the guide tube 35 and guide 36, as illustrated.

The piston rod 34 is circular, and is a close fit in a circular hole of the guide 36. In order to prevent rotation of the rod 34, the foot 32 is square and a close running fit in the clamp tube 33, which is square in section.

The piston head 37 comprises a support for a substrate 38 on which is provided a solder ball 39. Clamping jaws 40 are illustrated schematically.

In use the substrate 38 is rigidly clamped to the piston head 37 by suitable means, and the piston rod is allowed to retreat to the maximum extent, for example by contact between the underside of the piston head and the clamp tube 33. The jaws 40 are lowered and activated to grip the ball 39 tightly. Compressed air is applied via the inlet so as to lightly urge the piston rod upward as the jaws also accelerate upwardly. The piston rod 34 is arrested by abutment of the foot 32 on the underside of the guide 36, thus causing a high speed tensile force to be applied to the interface between ball 39 and substrate 40.

Adjustment of pressure and flow rate of compressed air can be adjusted to ensure that a light upward loading is applied to the substrate throughout the test.

In order to repeat the test, the piston rod is allowed to retreat, for example by closing off the supply of compressed air and allowing the pressure in the chamber to bleed away via an orifice. The jaws are then indexed over another ball to be tested, and the test is repeated.

As noted above, this embodiment has no obstruction above the piston head/platen 37, and accordingly a shorter length jaw tool can be used, which may be beneficial. It will be appreciated that in the embodiment of FIG. 1, the platen 18 may have an outward step for engagement by the arms 14, so that the arms 14 lie below the upper surface of the platen. In this case suitable clamping means are required for the substrates.

The invention claimed is:

1. A method of testing the bond strength of an electrically conductive ball adhered to a substrate, the method comprising the steps of:
    gripping the ball with a test tool,
    moving the ball in a direction substantially orthogonal to the plane of adherence of the ball while urging the substrate against the ball,
    abruptly halting the substrate, and
    measuring the force required to break the ball off of the substrate.

2. The method of testing according to claim 1 and including the preparatory step of clamping the substrate to a platen, whereby the platen is abruptly halted, thereby indirectly halting the substrate.

3. The method of testing according to claim 2 and including the step of providing a pneumatic ram to urge the substrate against the ball, and applying air under pressure to the ram in an amount sufficient to ensure a compressive load between the ball and substrate up to the time when the substrate is abruptly halted.

4. The method of testing according to claim 1 and including the step of providing a pneumatic ram to urge the substrate against the ball, and applying air under pressure to the ram in an amount sufficient to ensure a compressive load between the ball and substrate up to the time when the substrate is abruptly halted.

5. The method of claim 1, wherein abruptly halting the substrate comprises contacting the substrate against an abutment.

6. Apparatus for testing the strength of the bond between an electrically conductive ball and a substrate at a plane of adherence, the apparatus comprising:
    a gripper for gripping a ball adhered to a substrate;
    an apparatus for moving said gripper on an axis substantially orthogonal to the plane of adherence;
    an urging apparatus for urging the substrate on said axis towards said gripper, said urging apparatus adapted to move the substrate and ball along said axis;
    an abutment adapted to restrain the substrate while the apparatus for moving said gripper continues to move said gripper along said axis to break the ball off the substrate; and
    a force measuring apparatus configured to measure the force required to break the ball off the substrate.

7. The apparatus according to claim 6 wherein said urging apparatus comprises a pneumatic ram.

8. The apparatus according to claim 7 wherein said urging apparatus includes a platen for the substrate.

9. The apparatus according to claim 8 and further including a clamp device to releasably restrain the substrate on said platen.

10. The apparatus according to claim 9 wherein said abutment restrains the substrate by direct contact with said platen.

11. The apparatus according to claim 8 wherein said abutment restrains the substrate by direct contact with said platen.

12. The apparatus according to claim 7 wherein said abutment restrains the substrate by direct contact with said ram.

13. The apparatus according to claim 6 wherein said urging apparatus includes a platen for the substrate.

14. The apparatus according to claim 13 and further including a clamp device to releasably restrain the substrate on said platen.

15. The apparatus according to claim 14 wherein said abutment restrains the substrate by direct contact with said platen.

16. The apparatus according to claim 13 wherein said abutment restrains the substrate by direct contact with said platen.

17. The apparatus according to claim 6 wherein said abutment restrains the substrate by direct contact with the substrate.

18. A method of testing the strength of the bond between an electrically conductive ball and an electronic substrate at a ball-substrate interface, the method comprising the steps of:

securing the substrate to a platen;

positioning the substrate a sufficient distance from a stationary abutment to permit the substrate to be moved towards the abutment;

moving a test tool into engagement with the ball so that the test tool grips the ball;

moving the substrate and test tool in unison towards the abutment while urging the ball against the test tool and while preventing rotation of the substrate relative to the test tool;

causing the substrate to contact the abutment to abruptly halt the substrate;

continuing to move the test tool while still gripping the ball to break the ball off the substrate; and measuring the force required to break the ball off the substrate.

* * * * *

UNITED STATES PATENT AND TRADEMARK OFFICE
CERTIFICATE OF CORRECTION

PATENT NO. : 7,856,889 B2  
APPLICATION NO. : 10/599153  
DATED : December 28, 2010  
INVENTOR(S) : Benjamin Kingsley Stuart Peecock et al.

Page 1 of 1

It is certified that error appears in the above-identified patent and that said Letters Patent is hereby corrected as shown below:

Title Page
At (75), please change "Benjamin Kingsley Stuart Peecock, Suffolk (GB); Alan Norman Wiltshire, Essex (GB)" to -- Benjamin Kingsley Stuart Peecock, Suffolk (GB); Robert John Sykes, Essex (GB); Alan Norman Wiltshire, Essex (GB)--.

At (73), change "Nordson Corporation, Westlake, OH" to --Dage Precision Industries, Ltd., Buckinghamshire, United Kingdom--.

Signed and Sealed this
Twelfth Day of April, 2011

David J. Kappos
*Director of the United States Patent and Trademark Office*